United States Patent [19]

Rosdhy et al.

[11] Patent Number: 5,226,535
[45] Date of Patent: Jul. 13, 1993

[54] PACKAGE FOR ENDOSCOPIC SUTURE LOOP AND CANNULA

[75] Inventors: Constance E. Rosdhy, New Egypt, N.J.; Robert J. Cerwin, Pipersville, Pa.

[73] Assignee: Ethicon, Inc., Somerville, N.J.

[21] Appl. No.: 835,872

[22] Filed: Feb. 14, 1992

[51] Int. Cl.⁵ .............................. B65D 83/10
[52] U.S. Cl. .................... 206/363; 206/364; 206/63.3
[58] Field of Search ............ 206/63.3, 363, 364, 206/380, 383, 438

[56] References Cited

U.S. PATENT DOCUMENTS

| | | | |
|---|---|---|---|
| 3,206,018 | 9/1965 | Lewis et al. | 206/63.3 |
| 4,063,638 | 12/1977 | Marwood | 206/63.3 |
| 4,249,656 | 2/1981 | Cerwin et al. | |
| 4,253,563 | 3/1981 | Komarnycky | 206/63.3 |
| 4,332,322 | 6/1982 | Jaeschke et al. | 206/364 |
| 4,412,614 | 11/1983 | Ivanov et al. | |
| 4,483,437 | 11/1984 | Cerwin et al. | |
| 4,483,487 | 11/1984 | Cerwin et al. | |
| 4,491,218 | 1/1985 | Aday | |
| 4,496,045 | 1/1985 | Ferguson et al. | |
| 4,533,041 | 8/1985 | Aday et al. | |
| 4,549,649 | 10/1985 | Roshdy | |
| 4,555,016 | 11/1985 | Aday et al. | |
| 4,572,363 | 2/1986 | Alpern | |
| 4,574,957 | 3/1986 | Stead | |
| 4,615,435 | 10/1986 | Alpern et al. | |
| 4,884,681 | 12/1989 | Roshdy et al. | |
| 4,887,710 | 12/1989 | Roshdy et al. | |
| 4,946,043 | 8/1990 | Roshdy et al. | |
| 5,024,322 | 6/1991 | Holzwarth | 206/63.3 |
| 5,048,678 | 9/1991 | Chambers | |
| 5,082,112 | 1/1992 | Dunklee | |

*Primary Examiner*—David T. Fidei
*Attorney, Agent, or Firm*—Emil Richard Skula

[57] ABSTRACT

A foldable package for an endoscopic loop and cannula assembly. The package has a central panel having a pair of opposed major sides and a pair of opposed minor sides. The central panel also has a top tab extending from the top, minor side for retaining a suture loop, and a bottom tab foldably connected to the bottom minor side for retaining the proximal end of the cannula. A suture retaining panel is foldably connected to one major side of the central panel along the upper portion of that side. The package closure panel is foldably connected to the other major side of the panel, along the upper portion of the side, substantially opposite to the suture retaining panel. The cannula can be retained by a U-shaped slot in the bottom tab for receiving and engaging the proximal end of the cannula and a U-shaped slot in the suture retaining panel having at least one tab extending from the slot. The package may optionally have a gusset formed between the central panel and the bottom tab. The closure panel may be locked by a tab and a tab pocket. The tab and a tab pocket receive and engage the first tab in the central panel and suture panel along the fold line between the central panel and the suture retaining panel.

5 Claims, 5 Drawing Sheets

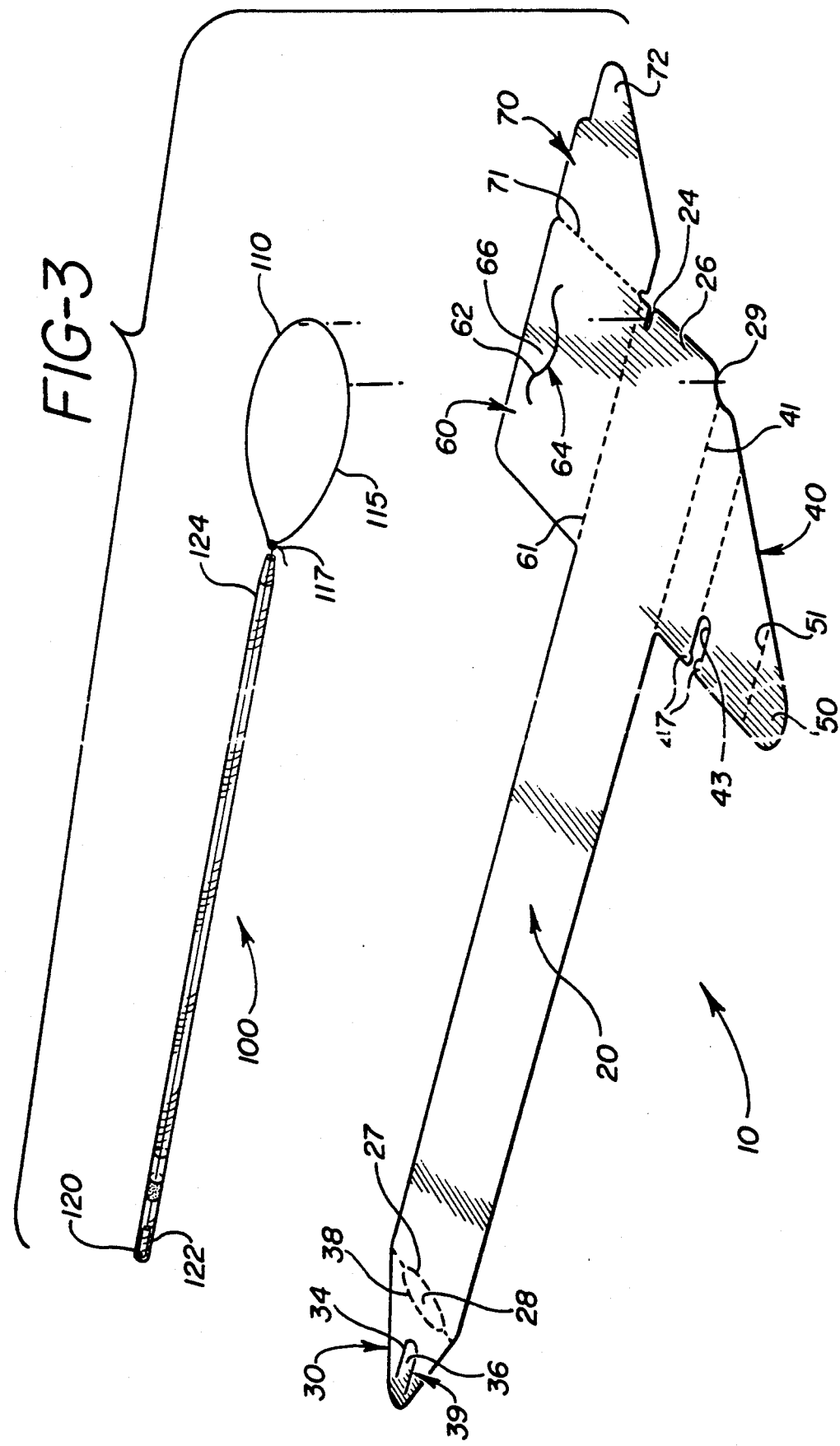

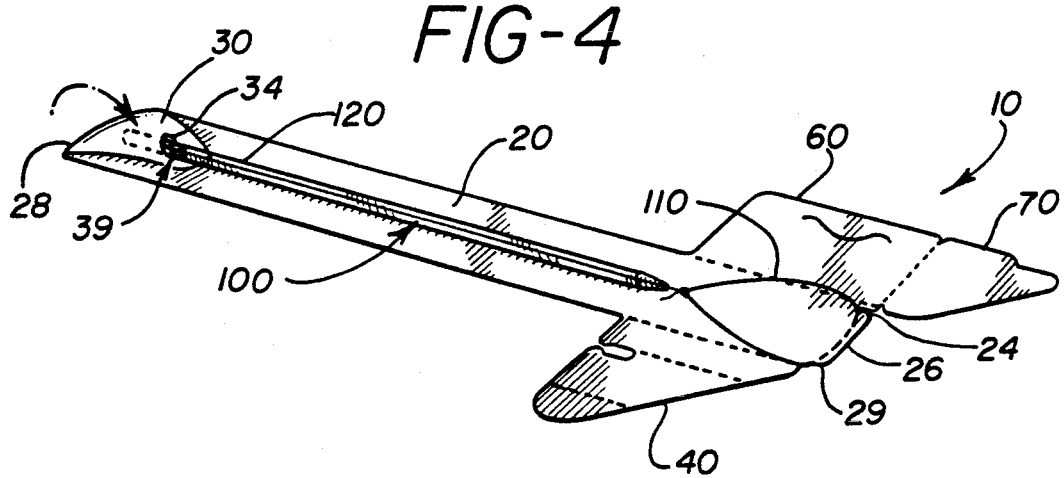
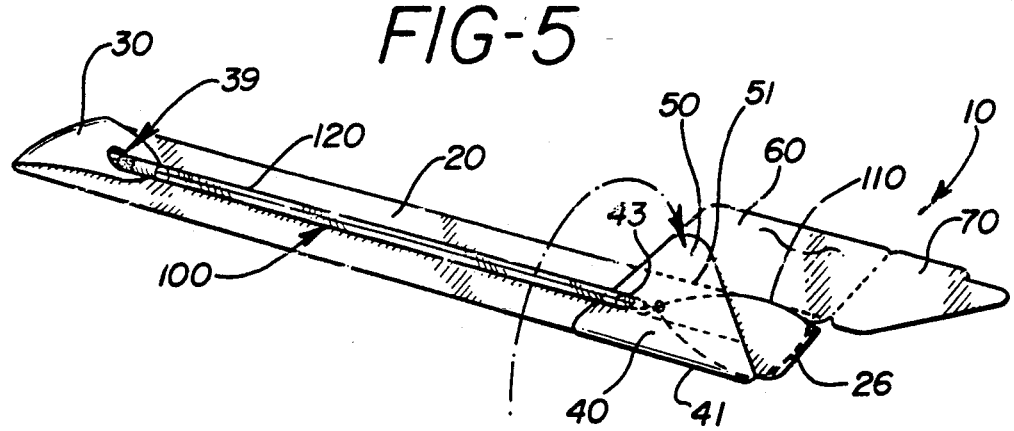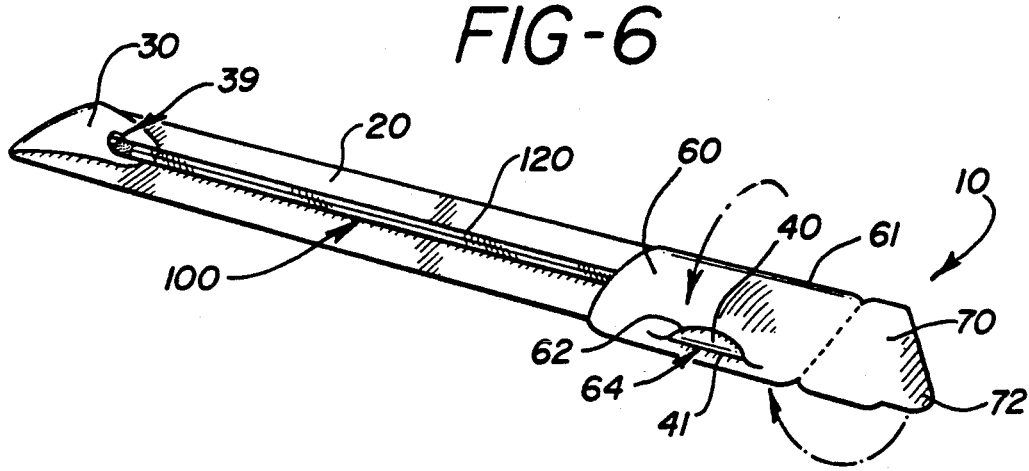

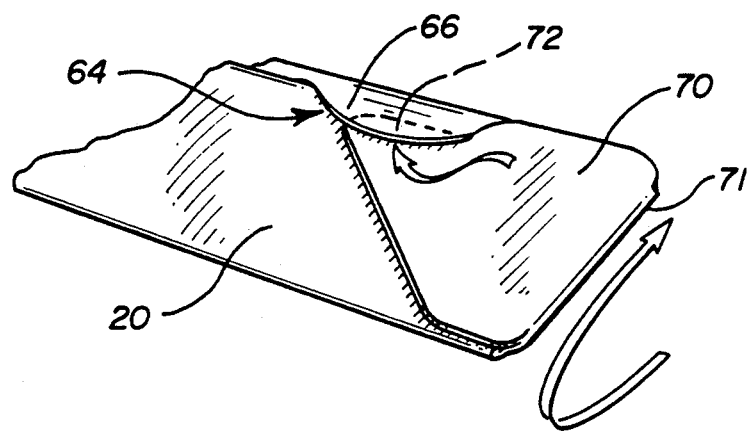
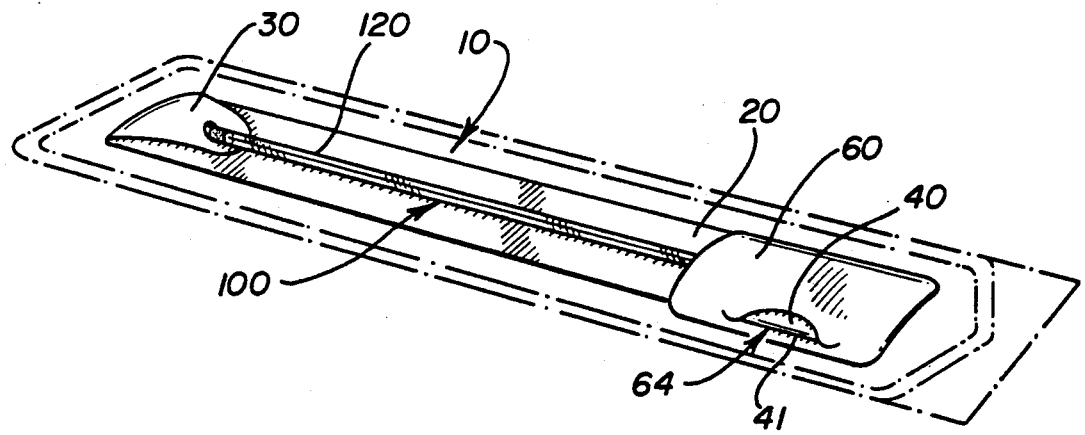

PACKAGE FOR ENDOSCOPIC SUTURE LOOP AND CANNULA

TECHNICAL FIELD

The field of art to which this invention relates is packaging, in particular, packaging for endoscopic sutures having a loop configuration and associated cannulas.

BACKGROUND OF THE INVENTION

The use of endoscopic surgical techniques (defined herein to include laparscopic and arthroscopic) is becoming widely accepted by the medical profession. The utilization of endoscopic surgical procedures has eliminated the need for radical incisions into the fascia and musculature of a patient in order to access a particular internal part of the patient's body. Typically, trocars are inserted into the body to penetrate through to body cavities such as the abdominal cavity. The trocars typically consist of two primary components, the first of which is an elongated piercing instrument, known as an obturator. The trocar assembly also contains a trocar cannula in which the trocar obturator is housed. The trocar cannula remains in the body cavity after the trocar obturator is removed and serves as a pathway to and from the body cavity.

Various types of endoscopic instruments may be inserted through the trocar cannula pathway, including endoscopes, stapling apparatuses, cutting and ligating apparatuses, and the like. As in most surgical procedures, it is frequently necessary to suture various sites within the body which are the subject of an endoscopic surgical procedure. Accordingly, various types of endoscopic sutures and cannula assemblies have been developed to satisfy this need. One particular type of endoscopic suture and cannula assembly is a suture having a loop and knot at a distal end of the suture, wherein the suture material also passes through a cannula. And, the other end of the suture is affixed to the proximal end of the cannula. In order to use the suture loop and cannula assembly in an endoscopic procedure, the loop, is inserted into a body cavity through a trocar cannula. The suture is manuevered with the cannula and looped about the target surgical area (e.g., a blood vessel) where the suture is to be employed. Next, the proximal end of the cannula is broken off, allowing the cannula to slide freely on the suture. Then, the the cannula is manipulated in a way so as to slide the cannula down along the suture, thereby pushing the knot down and tightening the loop until the targeted area is securely sutured. The cannula is then removed through the trocar cannula and the excess suture material is cut and removed by the surgeon.

It is essential that the endoscopic loop and cannula be packaged in such a manner that the loop retains its open configuration during shipping, handling, and, of course, during sterilization procedures. Many conventional sutures tend to have memories due to the nature of the materials from which they are made. A suture loop made from such a suture material, which becomes distorted in its package during sterilization, shipping, handling, etc., will typically tend to retain the distorted shape, possibly making the suture loop and cannula assembly unusable for an endoscopic surgical procedure. In addition, it is important that the endoscopic suture loop and cannula be easily removable from a package in a sterile section of an operating room without damaging the loop and cannula. Although there are existing packages for a suture loop and cannula assembly, these packages have the disadvantages of not allowing the looped cannula to be easily removed from the package, and of not readily retaining the loop in its open position. In addition, since a packaged loop and cannula assembly is typically placed into a plastic overwrap envelope prior to sterilization, it is critical that the plastic overwrap be protected from the cannula to prevent punctures and tears. Once the plastic overwrap is punctured or torn, the sterility of the loop and cannula is compromised and the device must typically be disposed of since it cannot be resterilized in a hospital environment. The packages of the prior art do not provide adequate protection for a plastic overwrap envelope.

What is needed in this art is a package for an endoscopic suture loop and cannula, which overcomes these deficiencies.

SUMMARY OF THE INVENTION

It is an object of the present invention to provide a package for an endoscopic suture loop and cannula which protects the cannula and suture during sterilization, handling, shipping and storage, but which allows the suture loop and cannula to be easily removed in an operating room.

It is a further object of the present invention to provide a package which maintains a suture loop in an open position.

It is yet another object of the present invention to provide a package for an endoscopic suture loop and cannula assembly which minimizes the possibility of tears or punctures to a plastic outer wrap.

It is a further object of the present invention to provide such a package which is easy and economical to manufacture.

A foldable package for an endoscopic suture loop and cannula assembly is disclosed. The package comprises a central floor panel having a top tab for retaining the suture loop and a bottom tab foldably connected to the bottom of the central floor panel for retaining the bottom of the cannula. The central floor panel has a pair of opposed major sides and a pair of opposed minor sides. A suture retaining panel is foldably connected to one major side of the central panel along the upper portion of that side. A package closure panel is foldably connected to the other major side of the central panel, along the upper portion of that side. The package closure panel is disposed substantially opposite to the suture retaining panel. The package has means for locking the cannula within the package and means for locking the package closure panel. The cannula locking means optionally comprise a U-shaped slot in the proximal tab for receiving and engaging the bottom end of the cannula, and, a U-shaped slot and at least one tab in the suture retaining panel for engaging the distal end of the cannula. The package optionally comprises a gusset formed between the bottom of the central panel and the bottom tab. The closure panel locking means comprises a tab and a tab pocket in the package closure panel. The closure locking panel optionally has a tab panel foldably attached to the upper side of the locking panel. The tab and tab pocket receive and engage the central panel and suture retaining panel along the fold line between the central panel and the suture retaining panel and the tab panel.

Other features and advantages of the invention will become more apparent from the following description and accompanying drawings.

BRIEF DESCRIPTION OF THE DRAWINGS

FIG. 3 is a perspective view of an endoscopic suture loop and cannula, and, the the package of the present invention prior to assembly.

FIGS. 4-7 are perspective views of the assembly of the package of the present invention.

FIG. 8 is a perspective view of an assembled package of the present invention containg an endoscopic suture loop and cannula assembly.

DESCRIPTION OF THE PREFERRED EMBODIMENTS

Figure 1:
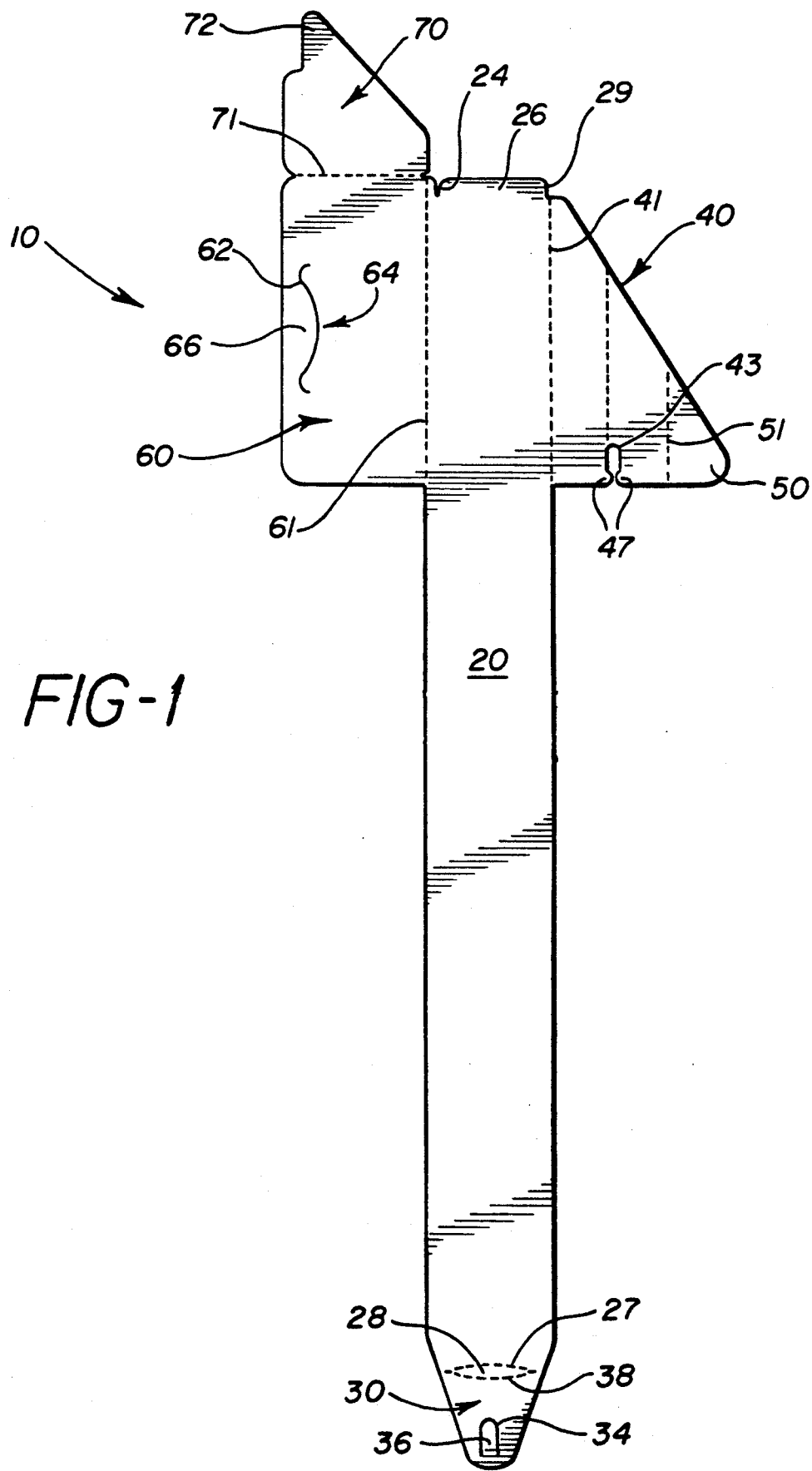
FIG. 1 is a plan view of the package of the present invention prior to folding.

Referring to FIG. 1 and FIG. 3, the package 10 of the present invention is seen to have a top, inner side and a bottom, outer side. The package 10 has central floor panel 20 for receiving the endoscopic suture loop and cannula. The central floor panel 20 is typically rectangularly shaped having a pair of substantially opposed major sides and a pair of substantially opposed minor sides. It will be appreciated that the central floor panel 20 may have other geometric configurations, for example, curved or sloping major sides. At the bottom minor side of the central floor panel 20 is located bottom tab 30 which is foldably connected to the central floor panel 20 along fold lines 27 and 38. Fold lines 27 and 38, which are coextensive in part, define gusset 28. Tab 30 has centrally located at its lower end U shaped slit 34 which defines tab 36. At the top minor side of the central floor panel 20 is tab 26 defined by U-shaped slot 24 on one side, and the offset top 29 of a first major side of the central panel 20 on the other side . It can be seen that the side 29 of tab 26 opposite slot 24 has been offset inwardly from the first major side of the central panel 20 so that the tab 26 is centered on central floor panel 20.

The central floor panel 20 has a loop retaining panel 40 foldably attached to the first major side along fold line 41. Loop retaining panel 40 is divided by fold line 45. The loop retaining panel 40 has along its lower edge U-shaped slot 43. At the bottom of U-shaped slot 43 are opposing tabs 47. Foldably attached to the loop retaining panel 40 along fold line 51 is tab 50.

Side panel or package closure panel 60 is foldably attached to the other major side of central floor panel 20 along fold line 61, and is disposed substantially opposite to loop retaining panel 40. Centrally located toward the outer edge of package closure panel 60 is slit 62 which forms tab 66 and tab pocket 64. Irregularly shaped tab panel 70 is foldably connected to the top of the side panel 60 along fold line 71. At the top of tab panel 70, there is a triangularly shaped tab 72.

Referring to FIG. 3, the suture loop and cannula assembly 100 is seen to have suture loop 110, suture 115, suture knot 117, and cannula 120. Cannula 120 has proximal end 122 and distal end 124.

In order to assemble package 10, as seen in FIG. 4, end flap 30 is initially folded up and inwardly along fold lines 27 and 38 to form gusset 28. Then tab 36 is pushed down and inwardly along slit 34 to form tab pocket 39. The loop and cannula assembly 100 is then positioned on top of central floor panel 20 so that the suture loop portion 110 of suture 115 is placed around tab 26 and the proximal end 122 of the cannula 120 is placed into tab pocket 39. Then the remainder of the assembly 100 is laid upon the top of central floor panel 20, with the proximal end 124 of cannula 120 and suture knot 117 centered on central floor panel 20. It can be seen that tab 26 retains the loop 110 while the tab pocket 39 retains the proximal end 122 of the cannula 120. Referring next to FIG. 5, loop retention panel 40 is then folded inwardly along fold line 41 and tabs 47 are displaced inwardly below the distal end 124 of cannula 120 so that the distal end 124 of the cannula 120 is engaged within U-shaped slot 43 by tabs 47. Next, as seen in FIG. 6, package closure panel 60 is folded along fold line 61 in an inward manner along with the tab panel 70 toward and over folded loop retaining panel 40 and central floor panel 20. As the side panel 60 is folded inwardly, it causes tab 50 to displace inwardly and down along fold line 51. Then, tab 66 is displaced behind the back of central floor panel 20 along fold line 41 causing the tab pocket 64 to receive and engage a section of the back, outer side of central floor panel 20 and a section of the back, outer side of loop retaining panel 40 along the fold line 41. Finally, as seen in FIG. 7, tab panel 70 is folded downwardly and inwardly toward the outer, back side of central floor panel 20 along fold line 71, and, the tab 72 is displaced into tab pocket 64 completing the assembly of the package 10. It should be noted that in FIG. 7 the package 10 has been rotated 180 degrees to the show the top of the back of package 10.

The assembled package 10 containing the endoscopic suture loop and cannula assembly 100 is seen in FIG. 8. The package 10 is shown inserted into a conventional plastic envelope 180 indicated by broken lines.

Referring to FIG. 8 and FIGS. 4-9, the package 10 is easily opened by pulling upwardly on side panel 60 and displacing the loop closure panel 40, central panel 20 and tab 72 out of the tab pocket 64. Next, tab 50 is pulled upwardly while grasping the cannula 120 and the central floor panel 20, thereby displacing the loop closure panel 40 and further displacing the distal end 124 of cannula 120 from the slot 43. Next, the cannula 120 is grasped and displaced distally in a direction parallel to the plane of central panel 20 such that the suture loop 110 is displaced from tab 26 and the proximal end 122 of the cannula 120 is displaced from slot 39, thereby freeing the loop and cannula assembly 100 from package 10.

Figure 2:
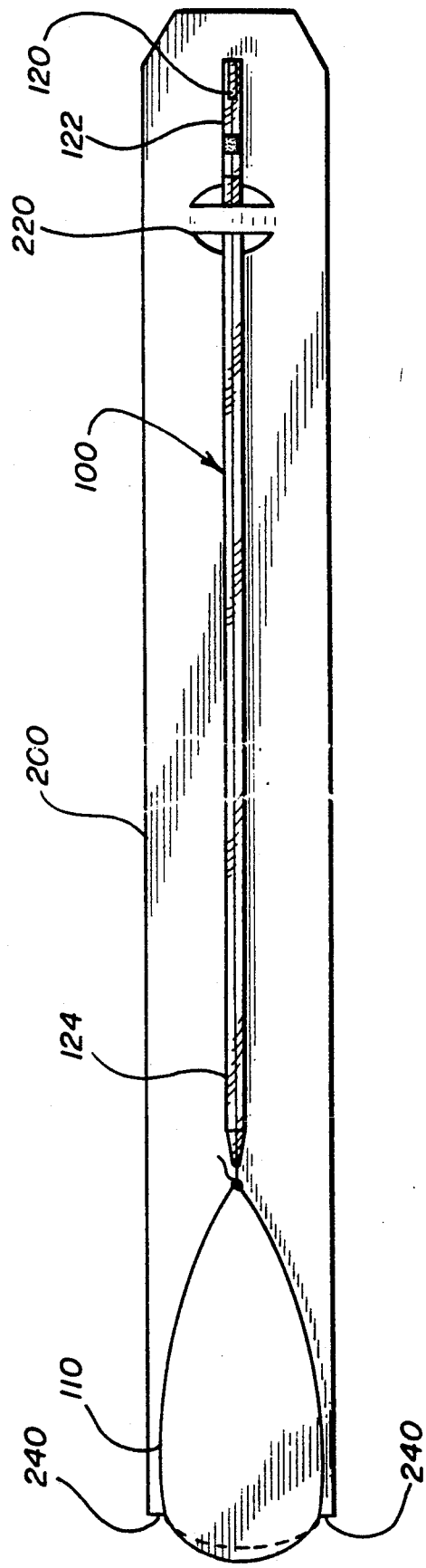
FIG. 2 is a plan view of a prior art package for an endoscopic suture loop and cannula assembly.

FIG. 2 illustrates an embodiment of the package 200 of the prior art containing a suture loop and cannula assembly 100. The proximal end 122 of cannula 120 is retained by loop 220. The suture loop 110 is retained and engaged in a friction fit by slits 240. It can be seen that the distal end 124 and the proximal end 122 of the cannula 120 are not contained within package 200 and it can be further seen that it is possible for the ends 122,124 to either puncture or tear a plastic overwrap envelope if the package is mishandled. Secondly, it can been seen that the cannula and loop assembly 100 is not readily removed from this package. In order to remove the assembly 100 from the package 200, the loop 220 must be torn or the cannula 120 must be manuevered through the loop 220, in either case this is a delicate and time consuming manuever. In addition the suture loop 110 must be forced out from the slits 240, once again requiring a delicate and time consuming manuever. Another disadvantage of the package 200 is that the distal end 124 of cannula 120 is not restrained and is free to move. This can result in distortion of the loop 110 or, as previously mentioned, the tearing or puncture of a plastic overwrap envelope 180.

The packages of the present invention may be constructed out of any material which is easily die cut and scored, and easily foldable, and which has sufficient strength and integrity to adequately protect the loop and catheter during sterilization, shipping, handling and storage. Such materials include conventional materials such as medical grade paperboard. It is particularly preferred to use a conventional, stiff paperboard having a thickness of about 0.008" to about 0.016". The paperboard, as previously mentioned, is preferably an appropriate medical grade. Other materials, including plastics, foils, and laminates combined with each other or with paper may also be used. The packages 10 are made using conventional equipment such as die cutting presses.

It will be appreciated by those skilled in the art that the size of the package 10 and the panels will vary in accordance with the size of the endoscopic suture loop and cannula assembly 100. The package 10 and the panels will be of sufficient size to effectively contain a particular suture loop and cannula assembly 100 as illustrated and described herein.

The package 10 of the present invention containing the suture loop and cannula assembly 100 is typically further packaged by insertion into a conventional plastic envelope 180 or a conventional foil packet which is then sealed. Such a plastic envelope typically is made from conventional materials such as TYVEK®, paper polyfoil, polyester copolymer, polypropylene copolymer, combinations thereof, and the like.

The packaged medical devices are typically sterilized using conventional sterilization equipment and processes. Examples of the sterilization processes which can be used on the endoscopic loop and suture cannula assemblies 100 packaged in the foldable package 10 of the present invention include conventional sterilization processes such as Co 60 irradiation, ethylene oxide, methylene bromide, and the like.

The one-piece package 10 of the present invention has many advantages. It is easy to manufacture out of conventional materials. The package 10 is extremely easy to assemble. The suture loop and cannula assembly 100 is retained and protected during sterilization, shipping, and handling. In particular, the loop 110 is maintained in an open configuration. The package 10 is easily opened in an operating room environment, and the cannula 120 and suture loop 110 are easily removed from the package 10 in one continuous motion. The risk of damaging the assembly 100 during removal from package 10 is substantially eliminated. The package 10 additionally prevents the cannula 120 from puncturing or tearing an outer plastic overwrap envelope.

Although this invention has been shown and described with respect to the detailed embodiments thereof, it will be understood by those skilled in the art that various changes and further detail thereof may be made without departing from the spirit and scope of the claimed invention.

What is claimed is:

1. A foldable package for an endoscopic suture loop and cannula assembly, comprising:
   a central floor panel, said panel having a top tab for retaining the suture loop and a bottom tab foldably connected to the bottom of the central floor panel;
   a loop retaining panel foldably connected to the bottom of the central floor panel;
   a package closure panel foldably connected to the central floor panel;
   a first U-shaped slot in the bottom tab for receiving and engaging a proximal end of the cannula;
   a second U-shaped slot, and at least one tab extending from the second slot; in the cannula retaining means for receiving and engaging a distal end of the cannula;
   a closure tab and a closure tab pocket in the closure panel, for locking the package such that the closure tab and closure tab pocket of the closure panel receive and engage the central panel and the loop retaining panel along the fold line between the central panel and the suture retaining panel; and,
   a gusset formed between the central panel and the bottom tab panel.

2. The package of claim 1 further comprising a tab panel foldably connected to the top of the package closure panel said tab panel received and engaged by the closure tab and closure tab pocket of the closure panel.

3. A foldable package for an endoscopic suture loop cannula assembly, comprising:
   a central panel, substantially rectangular in shape having a pair of opposed minor sides and a pair of closed major sides, said panel having a top tab extending from the top minor side for retaining the suture loop and a bottom tab foldably connected to the bottom of the central panel along the other minor side;
   a loop retaining panel foldably connected to one major side of the central panel along the upper portion of said side;
   a package closure panel foldably connected to the other major side of the central panel, along its upper portion, said package closure panel being disposed substantially opposite to the suture retaining panel;
   a first U-shaped slot in the bottom tab for receiving and engaging a proximal end of the cannula;
   a second U-shaped slot and at least one ear tab extending from the second slot in the suture retaining panel for receiving and engaging a distal end of the cannula; and
   means for locking the package closure panel to secure the package.

4. A foldable package for an endoscopic suture loop cannula assembly, comprising:
   a central panel, substantially rectangular in shape having a pair of opposed minor sides and a pair of closed major sides, said panel having a top tab extending from the top minor side for retaining the suture loop and a bottom tab foldably connected to the bottom of the central panel along the other minor side;
   a loop retaining panel foldably connected to one major side of the central panel along the upper portion of said side;
   a package closure panel foldably connected to the other major side of the central panel, along its upper portion, said package closure panel being disposed substantially opposite to the suture retaining panel;
   a first U-shaped slot in the bottom tab for receiving and engaging a proximal end of the cannula;

a second U-shaped slot and at least one ear tab extending from the second slot in the suture retaining panel for receiving and engaging a distal end of the cannula;

a first tab panel foldably attached to the top of closure panel;

a least one closure tab and closure tab pocket in the closure panel for locking the package, such that the closure tab and closure tab pocket of the closure panel receive and engage the central panel and the loop retaining panel along a fold line between the central panel and the loop retaining line between the central panel and the loop retaining panel and further receive and engage the first tab panel; and, a gusset formed between the top of the central panel and the top of the bottom tab.

5. The package of claim 3 further comprising a tab panel foldably connected to the top of the closure panel said tab panel received and engaged by the closure tab and tab pocket.

* * * * *

UNITED STATES PATENT AND TRADEMARK OFFICE
CERTIFICATE OF CORRECTION

PATENT NO. : 5,226,535
DATED : July 13, 1993
INVENTOR(S) : Constance E. Roshdy and Robert J. Cerwin It is certified that error appears in the above-indentified patent and that said Letters Patent is hereby corrected as shown below:

Title page, item [75],

Under the heading "Inventors",
    change "Rosdhy" to --Roshdy--

Signed and Sealed this

Twentieth Day of September, 1994

*Attest:*

BRUCE LEHMAN

*Attesting Officer*      *Commissioner of Patents and Trademarks*